US010966596B2

(12) United States Patent
Yamashita et al.

(10) Patent No.: US 10,966,596 B2
(45) Date of Patent: Apr. 6, 2021

(54) INSERTION DEVICE

(71) Applicant: OLYMPUS CORPORATION, Tokyo (JP)

(72) Inventors: Takashi Yamashita, Hachioji (JP); Yasuaki Natori, Akishima (JP); Takashi Suzuki, Hino (JP); Yoshitaka Umemoto, Hachioji (JP); Keijiro Omoto, Hachioji (JP); Fumiyuki Onoda, Tama (JP)

(73) Assignee: OLYMPUS CORPORATION, Tokyo (JP)

(*) Notice: Subject to any disclaimer, the term of this patent is extended or adjusted under 35 U.S.C. 154(b) by 359 days.

(21) Appl. No.: 15/951,612

(22) Filed: Apr. 12, 2018

(65) Prior Publication Data

US 2018/0242825 A1 Aug. 30, 2018

Related U.S. Application Data

(63) Continuation of application No. PCT/JP2016/080247, filed on Oct. 12, 2016.

(30) Foreign Application Priority Data

Oct. 16, 2015 (JP) .............................. JP2015-204733

(51) Int. Cl.
A61B 1/00 (2006.01)
A61B 1/005 (2006.01)
(Continued)

(52) U.S. Cl.
CPC ...... A61B 1/00156 (2013.01); A61B 1/00006 (2013.01); A61B 1/0016 (2013.01);
(Continued)

(58) Field of Classification Search
CPC .......... A61M 25/0116; G02B 23/2476; A61B 1/00156; A61B 1/00006; A61B 1/00039; A61B 1/0016; A61B 1/0052
See application file for complete search history.

(56) References Cited

U.S. PATENT DOCUMENTS 5,060,632 A * 10/1991 Hibino ............... A61B 1/00039
348/65
2014/0323805 A1 10/2014 Naito

FOREIGN PATENT DOCUMENTS

CN 104203076 A 12/2014
CN 104783846 A 7/2015
(Continued)

OTHER PUBLICATIONS

Chinese Office Action dated Jul. 23, 2019 in Chinese Patent Application No. 201680057717.7.
(Continued)

Primary Examiner — Timothy J Neal
Assistant Examiner — William B Chou
(74) Attorney, Agent, or Firm — Scully, Scott, Murphy & Presser, P.C.

(57) ABSTRACT

An insertion device includes a long and thin insertion section, a rotating housing that is provided to be rotatable about a longitudinal axis, a drive shaft that is connected to a motor rotating the rotating housing, and that transmits a rotation of the motor, a rotor that is provided at a distal-end side of the drive shaft and that is provided to be movable in relation to the rotating housing in axial direction of the insertion section, and that transmits the rotation to the rotating housing via a coating of the insertion section, a sensor that detects that the rotor moves a predetermined amount in either forward or backward direction relative to the axial direction of the insertion section, and a control unit
(Continued)

that controls, according to the detection by the sensor, a state of the motor including a positive rotation, a negative rotation, and rotation halt.

5 Claims, 8 Drawing Sheets

(51) Int. Cl.
    *G02B 23/24*     (2006.01)
    *A61M 25/01*     (2006.01)

(52) U.S. Cl.
    CPC ........ *A61B 1/00039* (2013.01); *A61B 1/0052* (2013.01); *A61M 25/0116* (2013.01); *G02B 23/2476* (2013.01)

(56) References Cited

FOREIGN PATENT DOCUMENTS

| | | |
|---|---|---|
| JP | H05-211993 A | 8/1993 |
| JP | 2005-328999 A | 12/2005 |
| JP | 2008-093029 A | 4/2008 |

OTHER PUBLICATIONS

International Search Report dated Dec. 27, 2016 issued in PCT/JP2016/080247.
English translation of International Preliminary Report on Patentability dated Apr. 26, 2018 together with the Written Opinion received in related International Application No. PCT/JP2016/080247.

\* cited by examiner

INSERTION DEVICE

CROSS-REFERENCE TO RELATED APPLICATIONS

This application is a Continuation Application of PCT Application No. PCT/JP2016/080247, filed Oct. 12, 2016 and based upon and claiming the benefit of priority from the prior Japanese Patent Application No. 2015-204733, filed Oct. 16, 2015, the entire contents of both of which are incorporated herein by reference.

BACKGROUND OF THE INVENTION

1. Field of Invention

The present invention relates to a rotary self-propelled insertion device.

2. Description of Related Art

Insertion devices such as endoscopic devices are commonly inserted endolumenally. One of these insertion devices is known as a rotary self-propelled insertion device. Rotary self-propelled insertion devices have, for example, a rotating housing called a power spiral tube having a spiral-shaped fin on the outer periphery of the insertion section. While the rotating housing is rotating, the fin of the rotating housing comes into contact with the endolumenal wall, causing stress to the same. By the stress, the insertion section propels itself either forward or backward. Such a rotary self-propelled insertion device is suggested, for example, in Jpn. Pat. Appln. KOKAI Publication No. 2008-93029.

BRIEF SUMMARY OF THE INVENTION

According to an aspect of the invention, there is provided an insertion device comprising: a long and thin insertion section; a rotating housing that is provided at an outer periphery of the insertion section, and that is provided to be rotatable about a longitudinal axis; a drive shaft that is provided inside the insertion section and that is further connected to a motor rotating the rotating housing, and that transmits a rotation of the motor, a rotor that is provided at a distal-end side of the drive shaft and that is provided to be movable in relation to the rotating housing in axial direction of the insertion section, and that transmits the rotation to the rotating housing via a coating of the insertion section; a sensor that detects that the rotor moves a predetermined amount in either forward or backward direction relative to the axial direction of the insertion section; and a control unit that controls, according to the detection by the sensor, a state of the motor including a positive rotation, a negative rotation, and rotation halt.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION OF THE INVENTION

Figure 1:
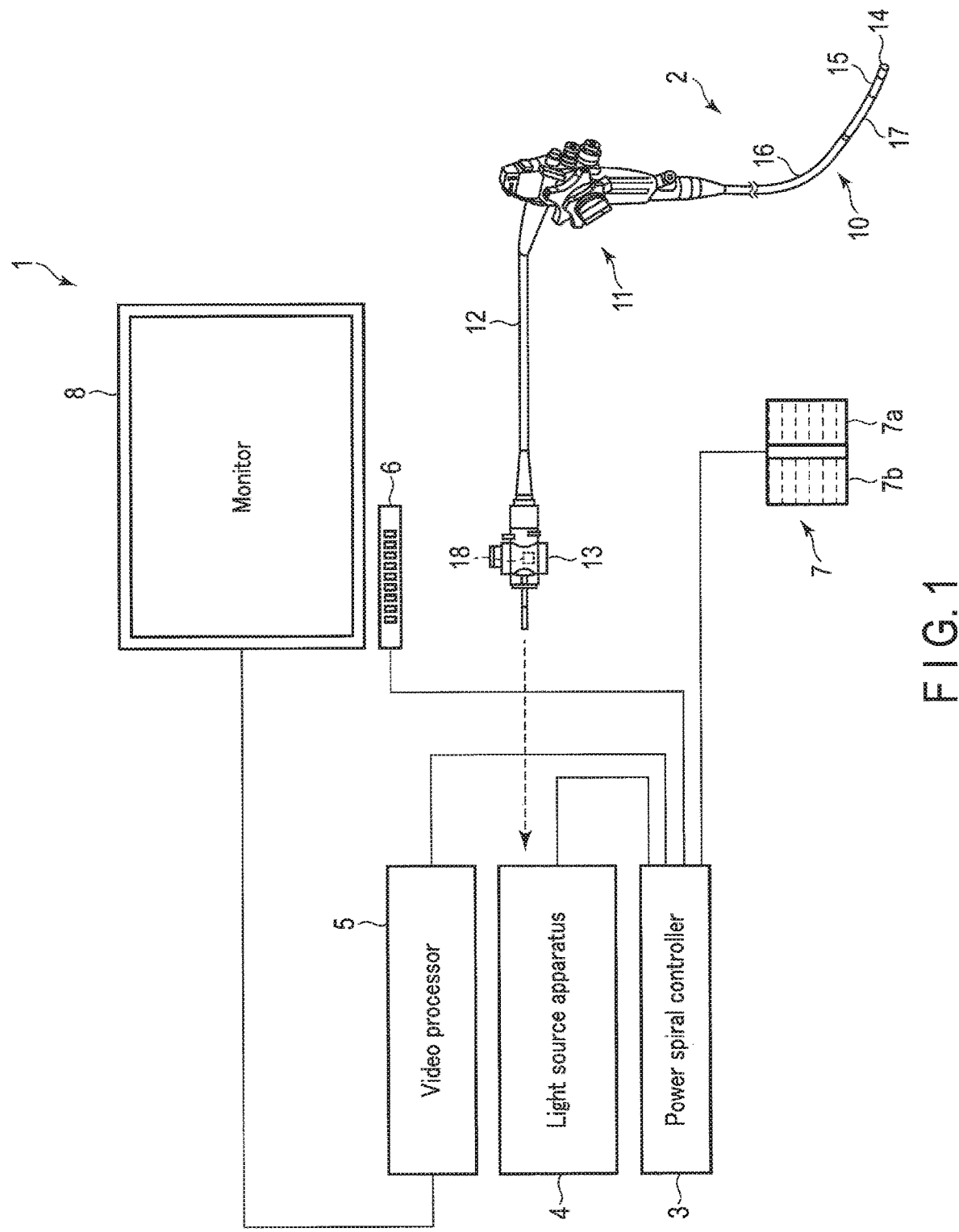
FIG. 1 is a schematic view of an endoscope system exemplary of an insertion device according to an embodiment of the present invention.

The embodiment of the present invention will here be described with reference to the drawings. FIG. 1 is a schematic overview of an endoscope system exemplary of an insertion device according to the embodiment of the present invention. As shown in the drawing, the endoscope system 1 comprises an endoscope 2, a power spiral controller 3, a light source apparatus 4, a video processor 5, an external display 6, a foot switch 7, and a monitor 8.

The endoscope 2 is a rotary self-propelled endoscope, and comprises an insertion section 10. The insertion section 10 is long and thin and configured to be inserted into a living body. The endoscope 2 further comprises an operation unit 11 mounted to the insertion section 10, for performing the various operations for the endoscope 2. The operation unit 11 is held by the operator. Hereinafter, the side of the distal end of the insertion section 10 shall be referred to as the "distal-end side", and the side to which the operation unit 11 of the insertion section 10 is provided shall be referred to as the "proximal-end side". Likewise, hereinafter, the direction from the distal-end side of the insertion section 10 along the proximal-end side shall be referred to as the "longitudinal direction".

The insertion section 10 comprises a distal end section 14, a bending section 15, and a flexible tubular section 16. The distal end section 14 is formed at the tip end of the insertion section 10, and it is configured not to curve. The distal end section 14 comprises an imaging device on its inside. The imaging element generates an imaging signal which is based, for example, on an object image at the distal-end side of the insertion section 10. The imaging signal that is generated by the imaging element is then transmitted to the light source apparatus 4 via a signal wire not shown in the drawings, which runs through both the insertion section 10 and the universal code 12. The bending section 15 is the portion formed at the proximal-end side of the distal end section 14, configured to actively curves according to the operations performed by an operating member not shown in the drawings, but provided at the operation unit 11. The flexible tubular section 16 is the portion formed at the proximal-end side of the bending section 15, configured to easily be bent by external force. The flexible tubular section 16 has the power spiral tube 17 mounted thereunto. The power spiral tube 17 is a tubular rotating housing made of, for example, a soft material such as rubber. The outer periphery of the power spiral tube 17 has a spiral-shaped fin provided along the longitudinal axis. The structures of the flexible tubular section 16 and the power spiral tube 17 shall further below be explained in greater detail.

The operation unit 11 comprises various operating members for enabling the operator to operate the endoscope 2. As an example, the operation unit 11 comprises, for example, a U/D-knob for causing the bending section 15 of the insertion section 10 to curve up and down, and an L/R-knob for causing the bending section 15 to curve left and right. When operating the U/D-knob and the L/R-knob, pushing and pulling the wires linked to the U/D-knob and the L/R-knob causes the bending section 1 to curve. The operation unit 11 further comprises, for example, a hand switch including a forward switch giving the command causing the insertion section 10 to move forward, and a backward switch giving the command causing the insertion section 10 to move backward. When the forward or backward switch is pushed, a command signal for causing the insertion section 10 to move forward or backward is transmitted to the power spiral controller 3. A motor 18 provided inside the operation unit 11 is then driven according to the command signal.

The operation unit 11 has the universal code 12 connected thereto, and the proximal-end side of the universal code 12 has the connector 13 provided thereto. The connector 13 is configured, for example, to be attachable to and detachable from the light source apparatus 4.

The power spiral controller 3 is, for example, a control unit constituted by an ASIC. The power spiral controller 3 controls the states of positive rotation, negative rotation and rotation halt of the motor 18 by controlling the drive power that is fed to the motor 18. The power spiral controller 3 controls, for example, the drive power of the motor 18 by causing the motor 18 to rotate at a rotation velocity according to the amount that the foot switch 7 is stepped on. The power spiral controller 3 further controls the drive power of the motor 18 by causing the motor 18 to rotate according to insert/remove operations of the insertion section 10. "Insert operation" here means that the operator pushes the insertion section 10 such that the insertion section moves in the direction of the distal end (forward). Similarly, "remove operation" here means that the operator removes the insertion section 10 such that the insertion section moves in the direction of the proximal end (backward). The insert/remove operations of the insertion section 10 do not only include direct push/pull operations of the insertion section 10, but also indirect push/pull operations of the insertion section 10 by pushing/pulling the operation unit 11.

The light source apparatus 4 has the endoscope 2 mounted thereunto. The light source apparatus 4 comprises alight source such as a white LED, emitting an illuminating light. The illuminating light emitted from the light source apparatus 4 is transmitted to the distal end of the insertion section 10 via alight guide not shown in the drawings, and is then emitted from the distal end of the insertion section 10. In this way, the interior of the test object is illuminated. In addition, the light source apparatus 4 transmits various signals fed via the connector 13 to the power spiral controller 3 and to the video processor 5.

The video processor 5 processes the imaging signal obtained by the imaging element of the insertion section 10. This process includes converting the imaging signal into a format which can be displayed on the monitor 8, such as a gradation correction process.

In FIG. 1, the power spiral controller 3, the light source apparatus 4, and the video processor 5 are shown as separate entities. However, they may also be configured as one.

The external display 6 is, for example, an LED display unit displaying the torque of the motor 18.

The foot switch 7 comprises a pedal for the operator to step on, and transmits a command signal to the power spiral controller 3 according to the amount that the pedal is stepped on. As an example, when the right-foot pedal 7a is stepped on, the foot switch 7 emits a command signal to the power spiral tube 17 to move forward. Similarly, when the left-foot pedal 7b is stepped on, the foot switch 7 emits a command signal to the power spiral tube 17 to move backward.

The monitor 8 is, for example, a common display device such as a liquid crystal display. The monitor 8 displays different kinds of images under the control of the video processor 5.

Figure 2:
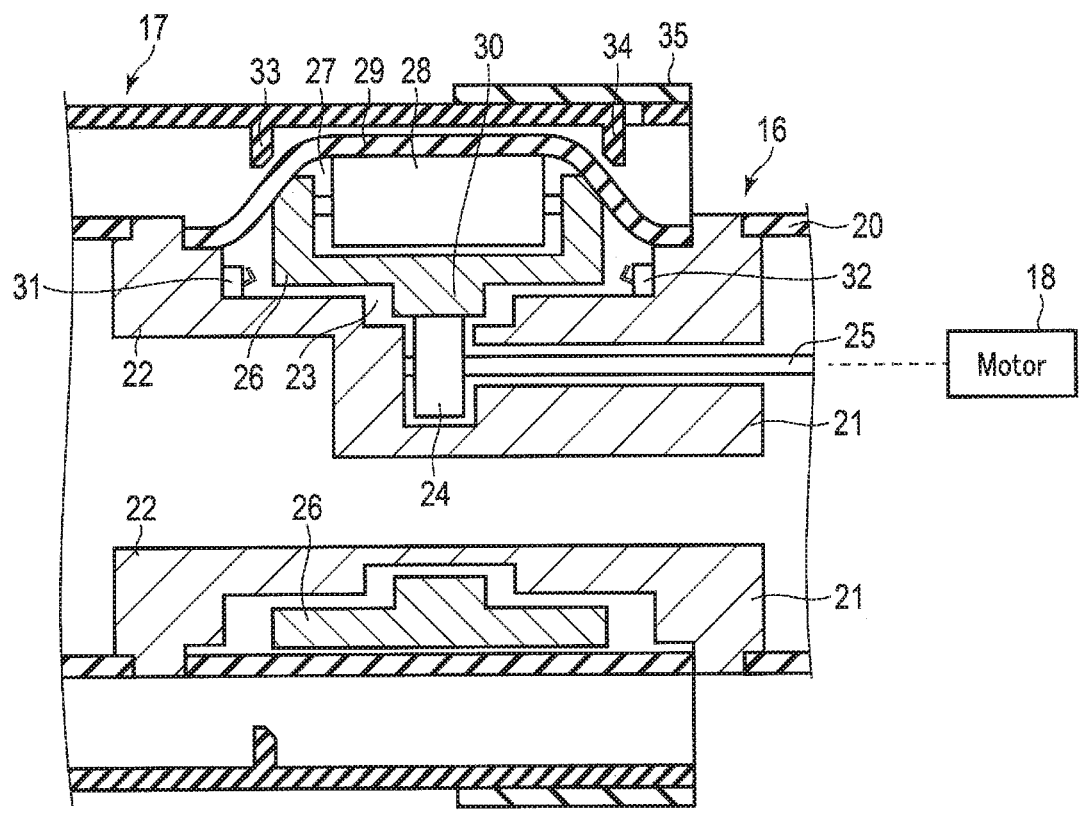
FIG. 2 is a cross-section view showing an example of a flexible tubular section and a power spiral tube according to the embodiment of the present invention.

The flexible tubular section 16 according to the embodiment shall here be described in greater detail. FIG. 2 is a cross-section drawing showing an example of the flexible tubular section 16 and the power spiral tube 17 according to the embodiment. The flexible tubular section 16 according to the embodiment has a mechanism built-in for detecting the insert/remove operations of the insertion section 10.

As shown in FIG. 2, the base 21 is formed at the flexible tubular section 16 which is in the position corresponding to the mounting position of the power spiral tube 17. The base 21 is, for example, engagingly fixated to an aperture provided in part of a coating 20 of the flexible tubular section 16. The distal end section of the base 21 has, for example, a supporting member 22 made of a metal arranged thereto. The distal end section of the supporting member 22 has the distal-end side of the flexible tubular section 16 linked thereto. The proximal end section of the supporting member 22 has the proximal-end side of the flexible tubular section 16 linked thereto.

The supporting member 22 is approximately tubular, and has a recess in one part as a cavity 23. The cavity 23 has a drive gear 24 and a rotary cylinder 26 arranged thereto. In the embodiment, the cavity 23 includes a space between the supporting member 22 and the rotary cylinder 26 about a size that allows the rotary cylinder 26 inside to slide a predetermined amount in the forward and backward direction of the insertion section 10. In addition, the supporting member 22 is restricted inside the flexible tubular section 16 at a force that allows the rotary cylinder 26 to slide in the forward and backward direction of the insertion section 10.

The drive gear 24 is mounted to a drive shaft 25 supported by the supporting member 22. The drive shaft 25 has the motor 18 mounted thereunto. This configuration allows the drive shaft 25 to rotate according to the rotation of the motor 18 about an axis which is parallel to the longitudinal axis of the insertion section 10. Likewise, the drive gear 24 rotates axially according to the rotation of the drive shaft 25, parallel to the longitudinal axis of the insertion section 10.

The rotary cylinder 26 that is the rotor is roughly tubular and has a recess in one part as a cavity 27. The cavity 27 has a roller 28 mounted thereunto. The outer periphery of the rotary cylinder 26 that includes the roller 28 is coated with a coating 29 of the flexible tubular section 16. The coating 29 is in contact with the roller 28 and its distal end and proximal end are adhered to the supporting member 22. The inner periphery of the rotary cylinder 26 has an inner gear 30. With this configuration, the supporting member 22 is inserted in the rotary cylinder 26, and the inner gear 30 is meshed with the drive gear 24. This configuration allows the rotary cylinder 26 to rotate according to the rotation of the drive gear 24 about an axis which is parallel to the longitudinal axis of the insertion section 10. The rotation of the rotary cylinder 26 is transmitted via the coating 29 to the power spiral tube 17. The roller 28 is provided such that the rotation of the rotary cylinder 26 is efficiently transmitted to the power spiral tube 17.

Here, in the embodiment, both the distal end section and the proximal end section of the rotary cylinder 26 are free ends so that the rotary cylinder 26 can slide in the forward and backward direction of the insertion section 10. On the other hand, the outer periphery of the rotary cylinder 26 may be restricted with a force to a predetermined extent within the rotational capability of the cylinder 26.

Furthermore, in the embodiment, the plane of the supporting member 22 opposing the plane of the distal-end side of the rotary cylinder 26 has a sensor 31 provided thereunto. Similarly, the plane of the supporting member 22 opposing the plane of the proximal-end side of the rotary cylinder 26 has a sensor 32 provided thereunto. The sensors 31 and 32 detect a predetermined amount of slide by the rotary cylinder 26. The sensors 31 and 32 shown in FIG. 2 are, for example, micro switches constituted of conductive parts and electrodes. The sensor 31 is configured to turn on when the rotary cylinder 26 moves backward a predetermined amount and comes into contact with the supporting member 22. Likewise, the sensor 32 is configured to turn on when the rotary cylinder 26 moves forward a predetermined amount and comes into contact with the supporting member 22. The output signals of the sensors 31 and 32 are transmitted to the light source apparatus 4 through the signal wire provided inside the universal code 12, and then from the light source apparatus 4 to the power spiral controller 3.

The inner periphery of the power spiral tube 17 according to the present has protrusions 33 and 34 formed thereunto. The protrusion 33 restricts a forward movement of the rotary cylinder 26 whenever the protrusion 33 contacts the coating 29 as a result of the supporting member 22 moving a predetermined amount in the forward direction of the insertion section 10. The protrusion 34 restricts a backward movement of the rotary cylinder 26 whenever the protrusion 34 contacts the coating 29 as a result of the supporting member 22 moving a predetermined amount in the backward direction of the insertion section 10. The protrusions 33 and 34 are, for example, constituted as one with the power spiral tube 17. The protrusions 33 and 34 may be made from a different material than the power spiral tube 17. FIG. 2 shows merely one protrusion 33 and one protrusion 34. In contrast, there may be a plurality of protrusions 33 and 34 along the circumferential direction of the power spiral tube 17.

Figure 3A:
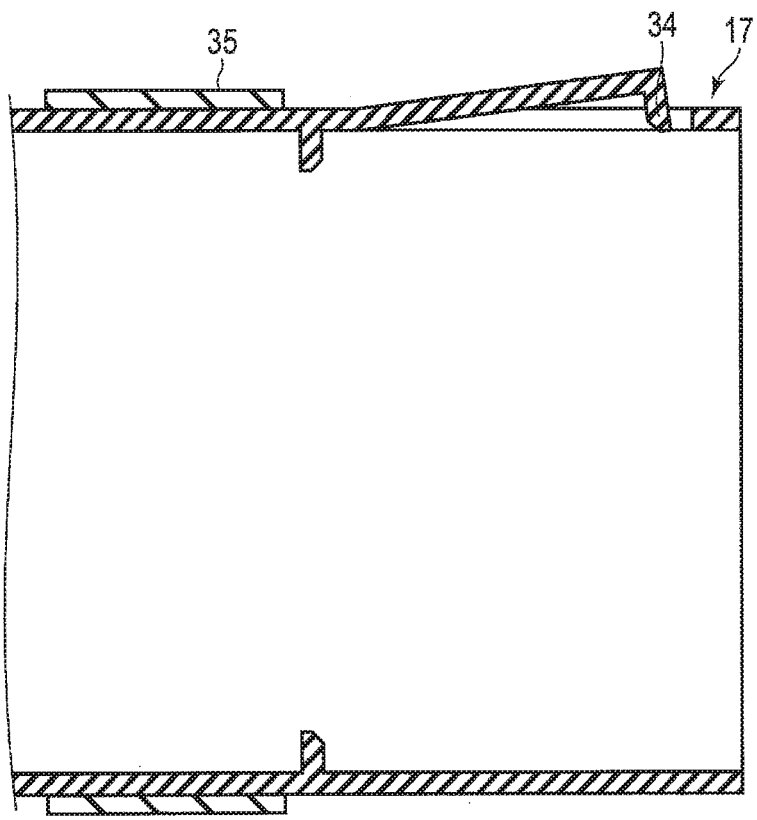
FIG. 3A shows the power spiral tube before a tube-holding tube is mounted.
Figure 3B:
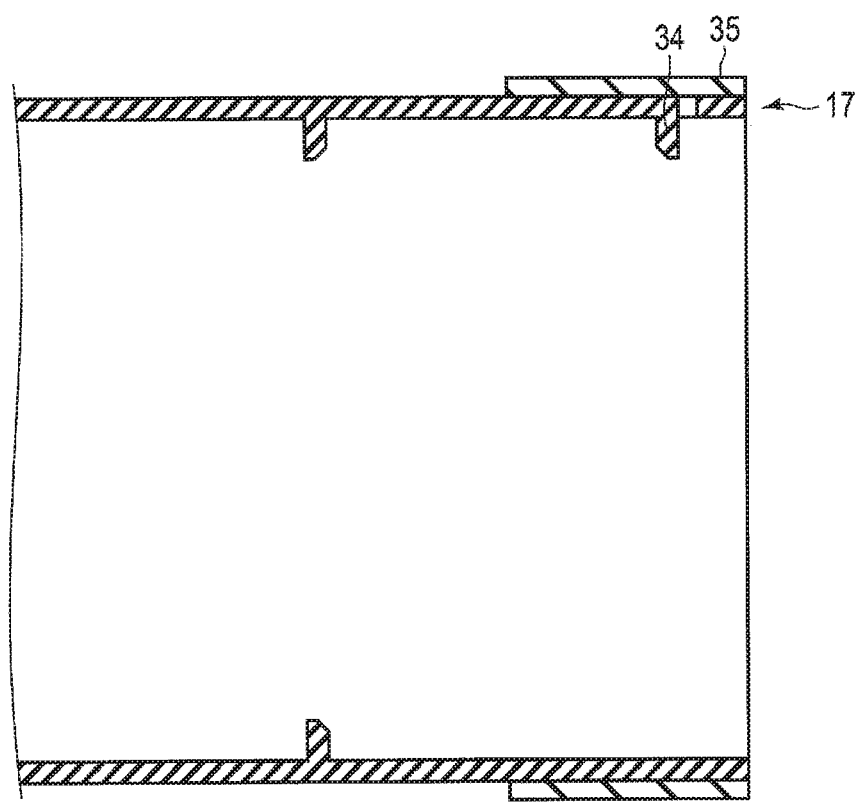
FIG. 3B shows the power spiral tube after the tube-holding tube is mounted.

A tube-holding tube 35 holds the power spiral tube 17 such that the power spiral tube 17 does not deviate from the flexible tubular section 16. The tube-holding tube 35 is configured slidably along the longitudinal direction of the power spiral tube 17. When mounting the power spiral tube 17 onto the flexible tubular section 16, first, the operator causes the tube-holding tube 35 to slide into a position where the protrusion 34 is not being pressed upon, as shown in FIG. 3A. The protrusion 34 is configured to lift when not receiving the pressing force from the tube-holding tube 35, as shown in FIG. 3A. As a structure for this, a structure may be considered where, for example, the part of the protrusion 34 is made elastic by a rubber. The protrusion 34 may also be lifted mechanically. In the state shown in FIG. 3A, the protrusion 34 does not butt the coating 29 of the flexible tubular section 16 when the power spiral tube 17 is mounted onto the flexible tubular section 16. Once the power spiral tube 17 is mounted at the position shown in FIG. 2, the operator causes the tube-holding tube 35 to slide into the position of the protrusion 34. The protrusion 34 then receives the pressing force from the tube-holding tube 35 and arrives at the position shown in FIG. 3B. There, the power spiral tube 17 is held. The power spiral tube 17 may here be constituted such that it does not deviate from the flexible tubular section 16. The structure of the protrusion 34 may then be different from the structure shown in FIGS. 3A and 3B.

Figure 4A:
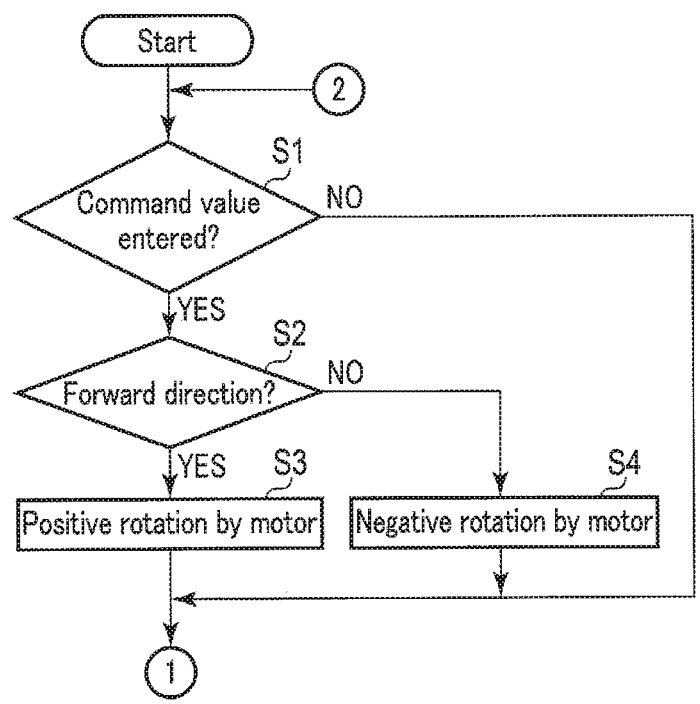
FIG. 4A is a flowchart of the rotation control of an endoscope motor.
Figure 4B:
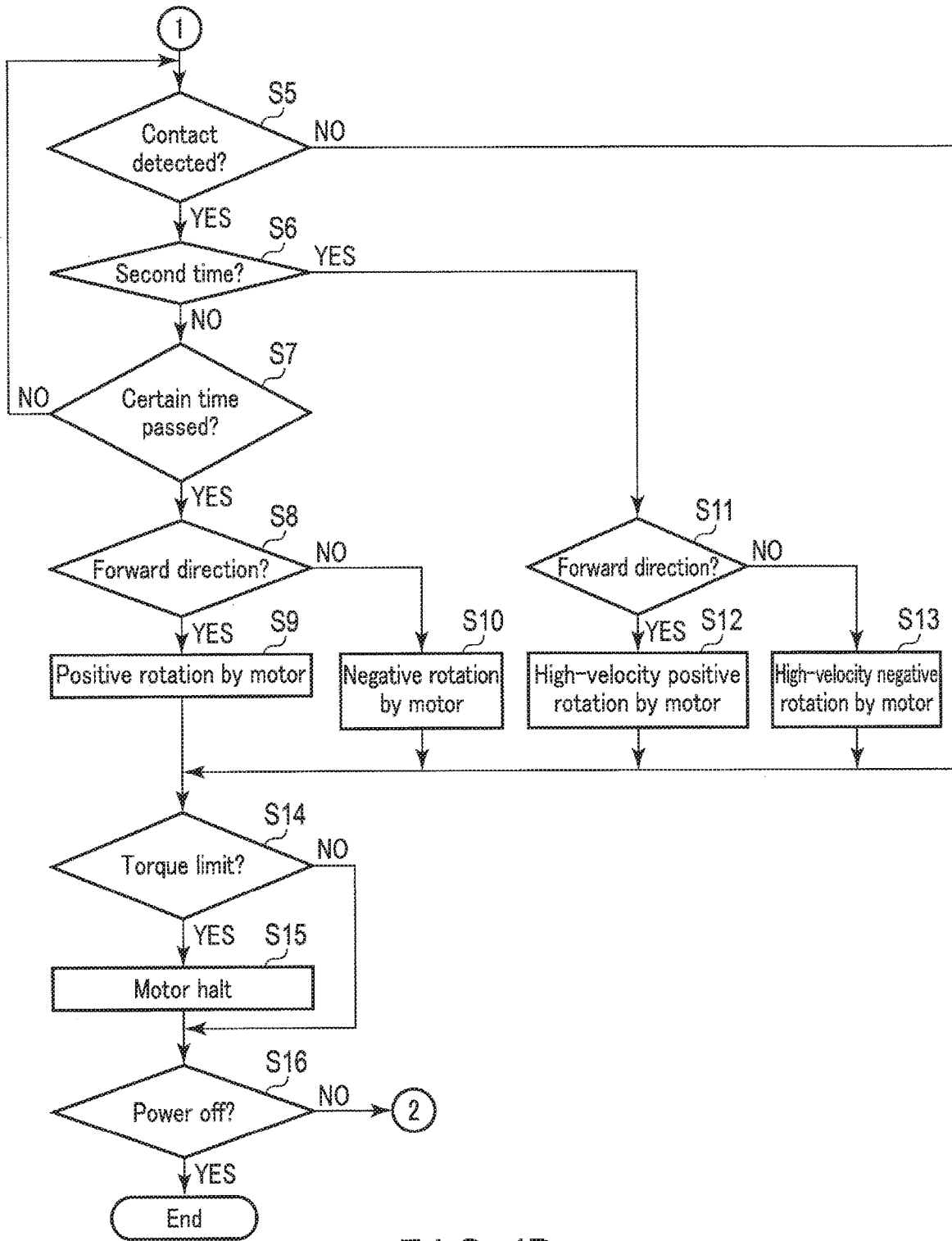
FIG. 4B is a flowchart of the rotation control of the endoscope motor.

The endoscope system 1 according to the embodiment shall here be described in detail. FIG. 4A and FIG. 4B are flowcharts of the rotation control of the motor 18 of the endoscope 2. The processes shown in FIG. 4A and FIG. 4B are performed by the power spiral controller 3.

As an example, upon turning on the endoscope system 1, the processes shown in FIGS. 4A and 4B commence. In step S1, the power spiral controller 3 determines whether or not a command signal causing the power spiral tube 17 to move forward or backward is fed from the operations by the operation unit 11 or the foot switch 7. If it is determined in step S1 that a command signal is fed, the process continues to step S2. If it is determined in step S1 that a command signal is not fed, the process continues to step S5.

In step S2, the power spiral controller 3 determines whether or not the insertion section 10 should be caused to move forward. If the command signal fed by the operation unit 11 or the foot switch 7 is a command to the power spiral tube 17 to move forward, it is determined in step S2 that the insertion section 10 should be caused to move forward. Likewise, if the command signal fed by the operation unit 11 or the foot switch 7 is a command to the power spiral tube 17 to move backward, it is determined in step S2 that the insertion section 10 should be caused to move backward. If it is determined in step S2 that the insertion section 10 should be caused to move forward, the process continues to step S3. If it is determined in step S2 that the insertion section 10 should be caused to move backward, the process continues to step S4.

In step S3, the power spiral controller 3 feeds the drive power for positive rotation of the motor 18 to the motor 18 at the velocity commanded by the operation unit 11 or foot switch 7. Through the positive rotation of the motor 18, the power spiral tube 17 is caused to likewise perform positive rotation. The positive rotation by the power spiral tube 17 generates a forward thrust unto the insertion section 10.

In step S4, the power spiral controller 3 feeds the drive power for negative rotation of the motor 18 to the motor 18 at the velocity commanded by the operation unit 11 or foot switch 7. Through the negative rotation of the motor 18, the power spiral tube 17 is caused to likewise perform negative rotation. The negative rotation by the power spiral tube 17 generates a backward thrust unto the insertion section 10.

In step S5, the power spiral controller 3 determines from the outputs by the sensors 31 and 32 whether or not contact between the rotary cylinder 26 and the supporting member 22 is detected. If it is determined in step S5 that contact between the rotary cylinder 26 and the supporting member 22 is detected, the process continues to step S6. If it is determined in step S5 that a contact between the rotary cylinder 26 and the supporting member 22 is not detected, the process continues to step S14.

Step S5 is a process for determining the insert/remove operations of the insertion section 10 performed by the operator. Below, the determination process of step S5 shall be described in detail. As an example, the case is assumed where the operator performs insert operations of the insertion section 10. When performing the insert operations, a force is exerted in the direction pushing the insertion section 10. Even if the force is exerted by the operator in the pushing direction, the power spiral tube 17 receives friction resistance from the body cavity and thus does not move instantaneously. The force exerted by the operator in the pushing direction is then transferred through the coating 29 and conveyed to the supporting member 22 and the rotary cylinder 26. As stated above, the supporting member 22 and the rotary cylinder 26 are configured to be slidable either in the forward direction or in the backward direction of the insertion section 10. As a result, the supporting member 22 and the rotary cylinder 26 move in the forward direction according to the force exerted by the operator in the forward direction. In this way, the relative positions of the rotary cylinder 26 and the protrusions 33 and 34 change.

Figure 5A:
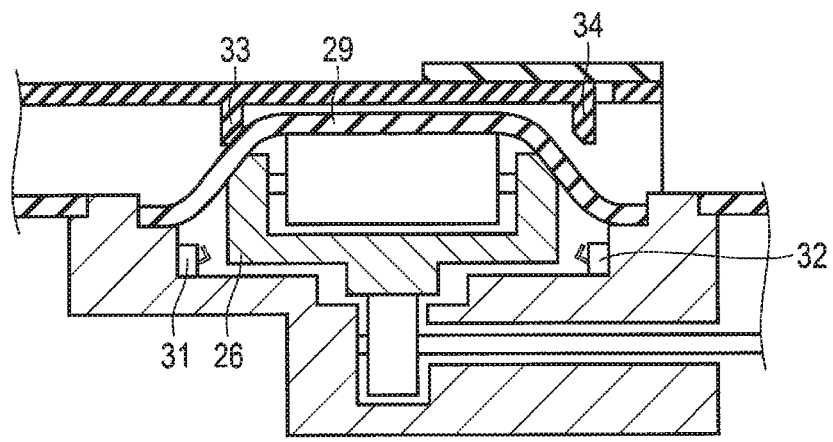
FIG. 5A shows a rotary cylinder when abutting the protrusion.
Figure 5B:
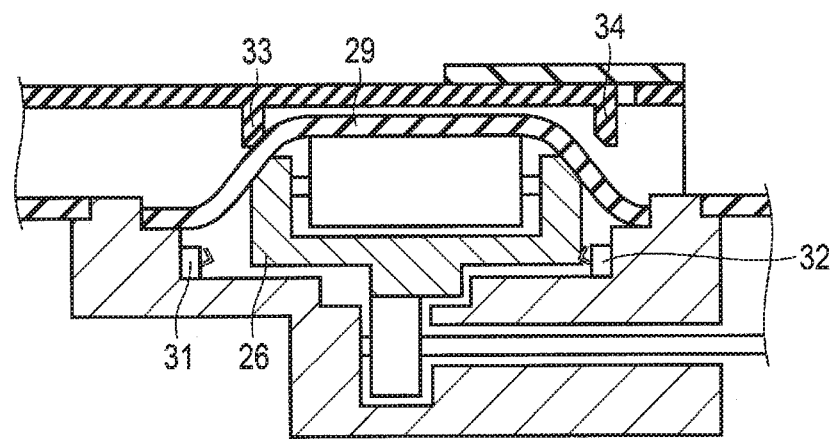
FIG. 5B shows the rotary cylinder when coming into contact with the supporting member.

When continuing the insert operations of the insertion section 10, the rotary cylinder 26 butts the protrusion 33 via the coating 29, as shown in FIG. 5A. When the insert operations of the insertion section 10 are further continued from this point, the rotary cylinder 26 comes to rest while only the supporting member 22 moves. In this way, the rotary cylinder 26 comes into contact with the supporting member 22, as shown in FIG. 5B. The sensor 32 then outputs a signal to the power spiral controller 3. The power spiral controller 3 recognizes from the signal that the operator has performed insert operations of the insertion section 10.

Figure 5C:
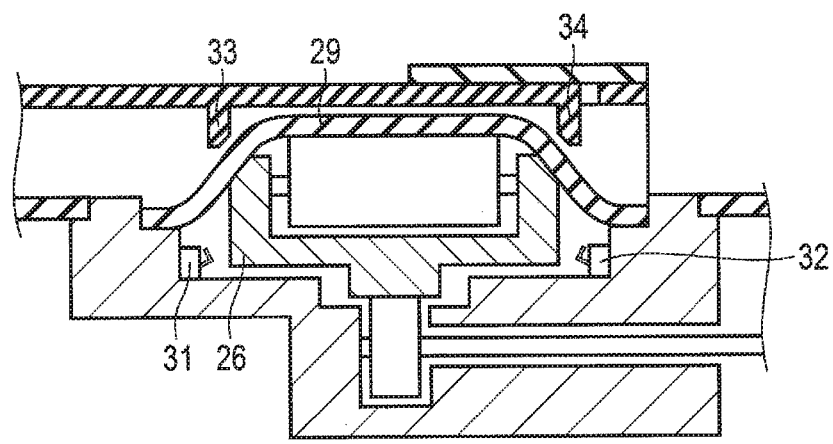
FIG. 5C shows the rotary cylinder when the contact with the supporting member is released.

When external force in the opposite direction is exerted from the state shown in FIG. 5B, the positional relationships between the protrusions 33 and 34, the rotary cylinder 26, and the supporting member 22 return to origin, as shown in FIG. 5C. Signal output from the sensor 32 to the power spiral controller 3 is then halted. In this way, the power spiral controller 3 recognizes that the operator stopped operating the insertion section 10.

Furthermore, when the operator performs remove operations of the insertion section 10, a force pulling the insertion section 10 is exerted. In that case, the sensor 31 which is, for example, a micro switch emits a signal to the power spiral controller 3. From the signal, the power spiral controller 3 recognizes that the operator has performed remove operations of the insertion section 10.

In step S6, the power spiral controller 3 determines whether or not a second contact between the rotary cylinder 26 and the supporting member 22 is detected. "Detecting a second contact" means detecting that the first contact was released and that a second contact is then established. In other words, when the contact is not released, it is determined that a second contact is not detected. If it is determined in step S6 that a second contact between the rotary cylinder 26 and the supporting member 22 is not detected, the process continues to step S7. When it is determined in step S6 that a second contact between the rotary cylinder 26 and the supporting member 22 is detected, the process continues to step S11.

In step S7, the power spiral controller 3 determines whether or not a predetermined short amount of time (for example 1 second) has passed since a contact between the rotary cylinder 26 and the supporting member 22 was detected. If it is determined in step S7 that a predetermined short amount of time has not passed, the process returns to step S5. If it is determined in step S7 that a predetermined short amount of time has passed, the process continues to step S8.

In step S8, the power spiral controller 3 determines whether or not the insertion section 10 should be caused to move forward. If it is detected that the operator performed insert operations, it is determined in step S8 that the insertion section 10 should be caused to move forward. Likewise, if it is detected that the operator performs remove operations, it is determined in step S8 that the insertion section 10 should be caused to move backward. If it is determined in step S8 that the insertion section 10 should be caused to move forward, the process continues to step S9. If it is determined in step S8 that the insertion section 10 should be caused to move backward, the process continues to step S10.

In step S9, the power spiral controller 3 feeds a drive power to the motor 18 causing the motor 18 to perform, for example, a positive rotation at a predetermined velocity. In this way, forward thrust is generated unto the insertion section 10, which supports the insert operations performed by the operator. After step S9, the process continues to step S14.

In step S10, the power spiral controller 3 feeds, for example, a drive power to the motor 18 causing the motor 18 to perform a negative rotation at a predetermined velocity. In this way, backward thrust is generated unto the insertion section 10, which supports the insert operations performed by the operator. After step S10, the process continues to step S14.

In step S11, the power spiral controller 3 determines whether or not the insertion section 10 should be caused to move forward. If it is detected that the operator performed insert operations twice, it is determined in step S11 that the insertion section 10 should be caused to move forward. Likewise, if it is detected that the operator performed remove operations twice, it is determined in step S11 that the insertion section 10 should be caused to move backward. If it is determined in step S11 that the insertion section 10 should be caused to move forward, the process continues to step S12. If it is determined in step S11 that the insertion section 10 should be caused to move backward, the process continues to step S13.

In step S12, the power spiral controller 3 feeds a drive power to the motor 18 causing the motor 18 to perform, for example, a positive rotation at a velocity higher than in step S9. The process of step S12 is intended for when two consecutive insert operations were detected. In that case, the operator is deemed to have a stronger intention to cause the insertion section 10 to move forward, thus accelerating the rotation velocity of the motor 18 such that the insertion section 10 is inserted quicker. After step S12, the process continues to step S14.

In step S13, the power spiral controller 3 feeds a drive power to the motor 18 causing the motor 18 to perform negative rotation at a velocity higher than in step S10. The process of step S13 is intended for when it is detected that two consecutive remove operations were detected. In that case, the operator is deemed to have a stronger intention to cause the insertion section 10 to move backward, thus accelerating the rotation velocity of the motor 18 such that the insertion section 10 is removed quicker. After step S13, the process continues to step S14.

In step S14, the power spiral controller 3 determines whether or not the state of torque limit is currently reached. "State of torque limit" means the state in which the torque of the motor 18 is at a predetermined value or higher. The state of torque limit is determined, for example, by determining that the motor current is at a predetermined value or higher. If it is determined in step S14 that the state of torque limit is currently reached, the process continues to step S15.

If it is determined in step S14 that the state of torque limit is currently not reached, the process continues to step S16.

In step S15, the power spiral controller 3 halts the power feed to the motor 18. In this way, unnecessary torque from the rotation of the power spiral tube 17 is prevented from being exerted unto the body cavity. After step S15, the process continues to step S16.

In step S16, the power spiral controller 3 determines whether or not the endoscope system 1 is turned off. If it is determined in step S16 that the endoscope system 1 is not turned off, the process returns to step S1. If it is determined in step S16 that the endoscope system 1 is turned off, the processes shown in FIGS. 4A and 4B terminate.

According to the embodiment, as explained above, the motor 18 is driven to cause the insertion section 10 to move forward when insert operations of the insertion section 10 are detected, and likewise, the motor 18 is driven to cause the insertion section 10 to move backward when remove operations of the insertion section 10 are detected, even when the operation unit 11 or the foot switch 7 is not operated. In this way, merely by the push/pull operations of the insertion section 10 performed by the operator, a thrust unto the insertion section 10 is generated in directions that are identical to the push/pull directions, according to the embodiment. As a result, the operator can perform the insert/remove operations intuitively and flawlessly.

According to the embodiment, during maintaining a state of detection of a contact between the rotary cylinder 26 and the supporting member 22, the motor 18 is controlled to reach a predetermined rotation velocity. When a contact in the same direction is detected twice within a short time, the motor 18 is controlled to rotate at a high velocity. In this way, it is possible to detect the intention of the operator and provide support such that the insert/remove operations can be performed quicker. When, according to the embodiment, operations to move the insertion section 10 in the same direction are detected twice within a short time, the motor 18 is controlled to rotate at a high velocity. The number of times is not limited to two. As an example, it is possible to control the motor 18 to accelerate the rotation of the motor 18 the larger the number of moving operations becomes within a predetermined time.

[Modification]

The sensors 31 and 32 according to the aforementioned embodiment are micro switches. The sensors 31 and 32 may be other than micro switches as long as they can detect a predetermined amount of movement of the rotary cylinder 26 that is the rotor. The sensors 31 and 32 can, for example, be linear encoders. Other than that, the sensors 31 and 32 may be strain gauges or pressure sensors that detect a pressing force within the contacting force between the rotary cylinder 26 and the supporting member 22.

Where the sensors 31 and 32 are sensors such as linear encoders or strain gauges which can detect the amount of movement by the rotary cylinder 26, it is possible to control the motor 18 to change its rotation velocity according to the amount of movement detected by the sensors. As an example, the motor 18 may be controlled to accelerate the rotation of the motor 18 the larger the amount of movement detected by the sensors becomes.

When, according to the aforementioned embodiment, operations to move the insertion section 10 in the same direction are detected twice within a short time, the motor 18 is controlled to rotate at a high velocity. In contrast, when the insertion section 10 stops being moved after a short time (for example after 0.1 seconds), the power spiral controller 3 may be configured to determine that the insertion section 10 is not being moved. In that case, the motor 18 is prevented from starting to be driven contrary to the intention of the operator in cases where, for example, vibrations or the like are exerted unto the insertion section 10 causing a contact to be established for just a short amount of time. Notice that it is possible to combine the aforementioned control for driving the motor 18 at a high velocity when operations to move the insertion section 10 in the same direction are detected twice within a short time, with the control for determining that the insertion section 10 is not moved when the insertion section 10 stops being moved within a short time.

The endoscope system 1 according to the present embodiment comprised both the hand switch of the operation unit 11 and the foot switch 7, but both the hand switch of the operation unit 11 and the foot switch 7 may be omitted. Also, the control according to the embodiment, namely to drive the motor 18 according to the detection of insert/remove operations of the insertion section 10 may be combined with the control to drive the motor 18 by operations of the hand switch of the operation unit 11 or by operations of the foot switch 7. As an example, it is possible to configure a switch for switching between control to drive the motor 18 according to the detection of insert/remove operations of the insertion section 10 and control to drive the motor 18 by operations of the hand switch of the operation unit 11 or by operations of the foot switch 7. Also, the rotation velocity of the motor 18 when insert/remove operations of the insertion section 10 are detected may be controlled differently than rotation velocity of the motor 18 when operations of the hand switch of the operation unit 11 or the foot switch 7 are detected. As an example, it is possible to set the rotation velocity of the motor 18 lower when insert/remove operations of the insertion section 10 are detected than when operations of the hand switch of the operation unit 11 or the foot switch 7 are detected. Then, when inserting the insertion section 10 until the vicinity of the intended position inside the body cavity, the operator operates the hand switch or foot switch 7 at a high rotation velocity of the motor 18. In the vicinity of the intended position, the operator can operate intuitively and the push/pull operations of the insertion section 10 are performed at a low rotation velocity of the motor 18. In this way, it is possible to insert the insertion section 10 until the intended position in a quick and accurate manner.

An example of the insertion device according to the embodiment is an endoscope system comprising a rotary self-propelled endoscope. However, an insertion device according to the embodiment does not necessarily have to be an endoscope system comprising a rotary self-propelled endoscope.

The present invention stands explained based on the aforementioned embodiment. However, the present invention shall not be limited to the aforementioned embodiment, and various modifications or applications may be made without departing from the spirit or scope of the general inventive concept of the present invention.

Each process according to the above-described embodiment may be stored as a program executable by a computer such as a CPU. Each process according to the above-explained embodiment may further be stored to the storage medium of an external storage device such as a memory card, a magnetic disc, an optical disc, or a semiconductor memory, and then be distributed via the same. Furthermore, it is possible to execute the aforementioned process by causing a CPU or the like to load the program stored in the storage medium of the external storage device, and then cause the loaded program to control the actions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
   an elongated insertion section;
   a spiral tube provided at an outer periphery of the insertion section, the spiral tube being provided to be rotatable about a longitudinal axis;
   a rotary cylinder rotatably provided on the insertion section and provided to be movable in relation to the spiral tube in a longitudinal direction of the insertion section, the rotary cylinder being configured to transmit rotation of the rotary cylinder to the spiral tube via a coating on the insertion section;
   a drive shaft provided inside the insertion section, the drive shaft transmitting a rotation of a motor to the rotary cylinder to rotate the rotary cylinder;
   a sensor for detecting movement of the rotary cylinder distally or proximally in the longitudinal direction of the insertion section; and
   a controller configured to control a state of the motor including a positive rotation, a negative rotation, and rotation halt based on the detection by the sensor.

2. The insertion device according to claim 1, wherein when the movement of the rotary cylinder is detected multiple times within a predetermined time period, the controller is further configured to control the motor to rotate at a velocity higher than during maintaining a state of detection of the movement of the rotary cylinder.

3. The insertion device according to claim 1, wherein when the movement of the rotary cylinder is not detected within a predetermined time period, the controller is further configured to control the motor to not to change the state of the motor.

4. The insertion device according to claim 1, wherein:
   the sensor is further configured to detect an amount of movement of the rotary cylinder either distally or proximally in the longitudinal direction of the insertion section; and
   the controller is further configured to control the motor to cause a rotation velocity of the motor to change according to the amount of movement detected by the sensor.

5. The insertion device according to claim 1,
   further comprising an operation unit operated by an operator, the operation unit being configured to assign, when operated, a command to rotate the motor, and
   wherein when the sensor detects that the rotary cylinder moves a predetermined amount distally or proximally in the longitudinal direction of the insertion section, the controller is further configured to decrease a rotation velocity of the motor as compared to a rotation velocity of the motor commanded by the operation unit.

* * * * *